United States Patent [19]

Wu et al.

[11] Patent Number: 5,851,579
[45] Date of Patent: Dec. 22, 1998

[54] AQUEOUS ENTERIC COATING COMPOSITIONS

[75] Inventors: Stephen Hong-Wei Wu, Kingsport; Warren Kent Hopkins, Piney Flats, both of Tenn.

[73] Assignee: Eastman Chemical Company, Kingsport, Tenn.

[21] Appl. No.: 947,121

[22] Filed: Oct. 8, 1997

Related U.S. Application Data

[60] Provisional application No. 60/009,646 Oct. 28, 1996.

[51] Int. Cl.$^6$ .............................. B05D 1/22; B05D 1/40; A61K 9/22; A61K 9/36
[52] U.S. Cl. .................... 427/2.21; 427/2.16; 427/2.19; 106/163.01; 106/168.01; 424/439; 424/457; 424/468; 424/480; 424/494; 514/781; 514/964; 514/961
[58] Field of Search ............................... 427/2.16, 2.21, 427/2.19, 213; 424/480, 468, 457, 439, 494; 523/334; 514/781, 964, 961; 106/163.01, 168.01

[56] References Cited

U.S. PATENT DOCUMENTS

| | | | |
|---|---|---|---|
| 4,013,820 | 3/1977 | Farhadieh et al. | 536/64 |
| 4,017,647 | 4/1977 | Ohno et al. | 427/2.16 |
| 4,026,932 | 5/1977 | Gross et al. | 260/29.6 H |
| 4,138,013 | 2/1979 | Okajima | 206/528 |
| 4,359,483 | 11/1982 | Kaetsu et al. | 427/2.21 |
| 4,716,041 | 12/1987 | Kjornaes et al. | 427/2.21 |
| 4,960,814 | 10/1990 | Wu et al. | 524/312 |
| 5,189,148 | 2/1993 | Akiyama et al. | 530/399 |
| 5,225,202 | 7/1993 | Hodges et al. | 424/480 |
| 5,346,542 | 9/1994 | Yosuke et al. | 106/194 |
| 5,505,983 | 4/1996 | Kamada et al. | 427/2.21 |
| 5,560,930 | 10/1996 | Maruyama et al. | 424/488 |
| 5,614,220 | 3/1997 | Hirakawa et al. | 424/480 |
| 5,681,581 | 10/1997 | Dunn | 424/468 |

FOREIGN PATENT DOCUMENTS

| | | |
|---|---|---|
| 377439 | 7/1990 | European Pat. Off. . |
| 541369 | 5/1993 | European Pat. Off. . |
| 57-032230 | 2/1982 | Japan . |
| 2057876 | 4/1981 | United Kingdom . |

OTHER PUBLICATIONS

"Polymers for Enteric Coating Applications", authored by G. Agyilirah and G. S. Banker, in a book, titled Polymers For Controlled Drug Delivery (P. J. Tarcha, ed., CRS Press, 1991) (No Month).

"Evaluation of Eastacyryl TM 30D and ammoniated HPMCP Blends for Synergistic Effects in an Enteric Coating Application", Pharm. Reserch, vol. 13, No. 9, Sep., 1996, p. 5191, Hopkins et al.

"PH–Sensitive Polymer Blends for Aqueous Enteric Coating Aplications," Proc. Int. Symp. Controlled Release Bioact. Mater. 24th, 1997, pp. 591–592 (No Month).

*Primary Examiner*—Diana Dudash
*Attorney, Agent, or Firm*—Michael J. Blake; Harry J. Gwinnell

[57] ABSTRACT

The present invention sets forth an enteric coating composition comprising a blend of a) an alkali-soluble acrylic latex polymer and b) an aqueous solution of ammonium or alkaline salts of cellulose polymers.

The invention also sets forth a method for preparing an enterically-coated dosage form and a method for preparing the present compositions.

17 Claims, No Drawings

AQUEOUS ENTERIC COATING COMPOSITIONS

FIELD OF INVENTION

This application claims the benefit of U.S. Provisional Application No. 60/029,646, filed Oct. 28, 1996.

This invention relates to an enteric pharmaceutical coating composition comprising a blend of alkali-soluble acrylic-based latex emulsions for enteric coating and ammonium or alkaline salts of cellulosic enteric coating polymers. The compositions described in this invention are useful for the enteric coating of pharmaceutical dosage forms.

BACKGROUND OF THE INVENTION

In preparing an oral pharmaceutical preparation, it is frequently desirable to coat the preparation with a polymeric material, commonly known as an enteric coating. An enteric coating is intended to prevent the active ingredients in the preparation, or dosage form, from disintegrating in the stomach, and to allow the active ingredient(s) to be released once the dosage form has passed into the small intestinal tract. Thus, polymeric materials that are suitable for enteric coating applications should be insoluble in a low pH medium typically having a value less than 3.5, but soluble in a higher pH medium typically having a value greater than 5.5. Thus, the objectives for using enteric coating materials in pharmaceutical dosage forms include a) to protect the stomach from the harmful effect(s) of an active ingredient, b) to protect the active ingredient from the adverse effect(s) of gastric fluid, c) to deliver an active ingredient to a particular region of the intestine, and d) to provide a sustained release dosage form to the gastrointestinal tract.

Polymers that are commonly used to enterically coat a pharmaceutical preparation include cellulosic materials such as cellulose acetate phthalate (C-A-P), cellulose acetate trimellitate (C-A-T), cellulose acetate succinate (C-A-S), hydroxypropyl methyl cellulose phthalate (HPMCP), hydroxypropyl methyl cellulose acetate succinate (HPMCAS) and carboxy methyl ethyl cellulose (CMEC). Other, non-cellulosic, polymers that are used as enteric coatings include copolymers of methacrylic acid and methyl methacrylate or ethyl acrylate, terpolymers of methacrylic acid, methacrylate, and ethyl acrylate, and polyvinyl acetate phthalate (PVAP).

To apply an enteric coating onto a dosage form substrate, an organic solvent may be used as a vehicle for coating the polymers onto the dosage form. Examples of such solvents include acetone, methanol, ethanol, isopropyl alcohol, ethyl acetate, methylene chloride, or mixtures thereof. Organic solvent-based enteric coating preparations usually provide consistent film quality, reliable in vitro and in vivo dissolution characteristics, and good shelf stability. Because of environmental and safety concerns and the cost of solvent recovery, however, the use of organic solvents as vehicles is considered less desirable than the use of water as the vehicle in a coating process.

One may avoid using organic solvents by using aqueous coating systems such as acrylic enteric polymers in latex form, aqueous dispersions of cellulosic enteric polymers (known as pseudolatices) and aqueous ammonium salt solutions of the cellulosic enteric polymers HPMCP or C-A-P. However, these aqueous coating systems exhibit drawbacks in both preparing the dosage form and in its final performance. Specifically, major problems associated with using latex emulsions of enteric acrylic polymers include:

a. coagulation of the latex emulsion when subjected to shearing forces, b. coating process interruption due to plugging of spray nozzles by coagulated latex, c. sensitivity of latex particles to multivalent metal cations, coating bed temperature and atomizing air pressure, d. tackiness of the coating during the coating process, e. formation of fragile coating films relative to cellulose-type coatings, and f. inconsistent dissolution characteristics of the preparation after a period of storage because of continual coalescencing of the coating film at the storage conditions.

The major problems associated with pseudolatices (i.e., aqueous dispersions of cellulosic enteric polymers) are worse than alkali-soluble acrylic latex emulsions. This is because the dispersed cellulosic polymers usually have a particle size that is much larger than latex particles, and the dispersed particles require a greater quantity of plasticizer to induce film formation.

Further, a major drawback for using aqueous solutions of ammonium or alkaline salts of cellulosic enteric polymers is the instability and high water permeability of the resultant film. Residual moisture in the substrate and the residual ammonia or alkaline salt moieties in the cast film slowly hydrolyze the acid functional phthalyl, succinyl, trimellityl moieties of the polymer from the cellulose backbone. Hydrolysis can occur upon exposure to accelerated storage conditions such as 40° C. and 75% relative humidity (RH) or at atmospheric conditions over time. The dissolution characteristics of the preparation vary as hydrolysis proceeds. In addition, the film exhibits high permeability to gastric fluid so that the active ingredients may be adversely affected by the penetrating gastric juices. Another disadvantage is that the aqueous salt solution exhibits a relatively high viscosity, and must be prepared at a lower solid concentration typical of emulsions to allow the solution to be sprayable.

The use of enteric coating polymers for dosage form preparations is known. See, for example, "Polymers For Enteric Coating Applications," authored by G. Agyilirah and G. S. Banker, in a book, titled "Polymers For Controlled Drug Delivery" (P. J. Tarcha, ed., CRS Press, 1991).

U.S. Pat. No. 4,017,647 describes a method for providing enteric coatings on solid dosage forms via conversion of water-soluble polymeric salt into water-insoluble polymeric acid. A dosage form was first coated with alkali metal, ammonium or amine salts of an enteric polymer and then the coated dosage form was brought into contact with a strong inorganic acid so that the enteric polymeric substance was converted into a water-insoluble acid form.

U.S. Pat. No. 4,138,013 describes formation of enteric capsules by dip-molding of a homogeneous film-forming mixture comprising gelatin and ammonium salt of an enteric coating polymer such as HPMCP and C-A-P ammonium salts. An alternate capsule combines gelatin and a copolymer of methacrylic acid and methacrylic acid alkyl ester. U.S. Pat. No. 4,013,820 describes a process of making powdered ammonium, alkali metal salts in an alcohol of 1–3 carbon atoms.

Japanese Patent JP 57032230 describes a suppository having ammonium salts and alkali metal salts of enteric polymers. The suppository, which contains agar, is highly water-soluble.

The present invention is a coating composition that overcomes the disadvantages described in the aqueous enteric coating systems. The invention comprises a blend of an alkali-soluble acrylic polymer latex emulsion and an ammonium or alkaline salt of cellulosic enteric polymers to form a coating composition providing unexpected and improved performance over either the individual acrylic latex or the ammonium salt system alone.

SUMMARY OF THE INVENTION

The present invention sets forth an enteric coating composition comprising a blend of a) an alkali-soluble acrylic latex polymer and b) an aqueous solution of ammonium or alkaline salts of cellulose polymers.

The invention also sets forth a method for preparing an enterically-coated dosage form, and a method for preparing an enteric coating composition.

DETAILED DESCRIPTION OF THE INVENTION

The coating compositions of the present invention are insoluble in a low pH environment such as the stomach, where the fluid has a pH value normally less than about 3.5, but dissolve rapidly or swell sufficiently to disintegrate in a high pH environment, such as intestinal fluid, which has a pH value normally greater than about 5.0. The compositions of the present invention are useful as enteric coatings for oral dosage forms including granulated or tableted medicaments, microparticles, or soft or hard capsules. The compositions can be applied onto the objects for coating using water as a coating vehicle. The compositions of the present invention comprise a blend of alkali-soluble acrylic polymer and ammonium or alkaline salts of cellulosic enteric polymers, and other optional coating additives, which can overcome disadvantages associated with the alkali-soluble acrylic polymer latexes or ammonium salts of cellulosic enteric polymers when they are used alone without the presence of the other.

We have discovered that a blend of 1) an alkali-soluble acrylic latex polymer and 2) an aqueous solution of ammonium or alkaline salts of cellulosic enteric polymers exhibits unexpected and desirable characteristics useful for enteric coating applications. During blending, the acrylic latex particles are softened, and intimately associated with and surrounded by ammonium or alkaline salts of cellulosic enteric polymers in an aqueous medium. Thus, the ammonium or alkaline salts of cellulosic enteric polymers serve as a protective colloid for the latex particles so that the blend exhibits unique properties suitable for aqueous enteric coating applications.

The resulting blend is much less sensitive to heat and high shearing forces than the acrylic latex alone. In addition, the blend exhibits a broad, stable viscosity range that can minimize settling of mineral additives such as talc and aluminum lakes or other particulate additives in the coating dope. Further, we have found that even a small amount of acrylic enteric latex may decrease significantly the solution viscosity of the ammonium salt solution of cellulosic enteric polymers. Thus, solutions of ammonium salts of cellulose enteric polymers in the presence of acrylic enteric latex can be applied at a higher concentration without suffering the effect of high solution viscosity.

Another aspect of this invention is that the blends, in a broad composition range, exhibit essentially a constant pH value, which is very close to the pKa value of the acidic functional groups. It is known that adding a small amount of base as an annealing agent to latex-based coating dopes will partially neutralize the acrylic polymers, while maintaining the integrity of the latex emulsion. This enhances the coalescence of emulsion particles in the film-forming process on the surface of a substrate. Thus, ammonium salts of a cellulosic enteric polymer serve essentially as a polyelectrolyte base and an annealing agent for the latex, and also provide a layer of protection for the latex particles against pH shocks. The resulting blend is relatively insensitive to dilution and pH shock. It easily coalesces on the surface of a substrate.

It was discovered that the coating films formed from the blends exhibit a consistent glass transition temperature, which is lower than the glass transition temperature (Tg) of an acrylic enteric film. In the absence of other ingredients such as plasticizers, the Tg is about 112° C. This indicates that alkali-soluble acrylic polymer latex and ammonium salts of cellulosic enteric polymers form a miscible polymeric blend after ammonia is evaporated. The lower Tg of the blend forms a more flexible film compared with the film made from the acrylic latex itself and exhibits flexibility typically shown by ammoniated cellulosic enteric polymers.

In accordance with this invention, alkali-soluble acrylic polymer latex emulsions are latex emulsions of copolymers of acrylic acid monomers and acrylate monomers at various ratios, typically at 1:1 to 1:2 ratios. Typical acrylic enteric copolymers are copoly(methacrylic acid/ethyl acrylate 1:1), copoly(methacrylic acid/methyl methacrylate 1:1 or 1:2), or polymers made of a combination of methacrylic acid, methyl methacrylate and ethyl acrylate at a desired ratio. A 30% aqueous dispersion of the copolymer of ethyl acrylate and methacrylic acid is commercially available from Rohm Pharma GmbH, Damstadt, Germany, under the trade name EUDRAGIT® L 30 D, from BASF GmbH, Germany, under the name Kollicoat® MAE 30, and from Eastman Chemical Company, Kingsport, Tenn., under the name Eastacryl® 30 D. These products typically exhibit a molecular weight (Mw) of 200,000, a pH value about 2.5, and a viscosity about 6–7 cps.

Common cellulosic enteric polymers useful as the aqueous solution of ammonium or alkaline salts of cellulosic polymers include C-A-P having phthalyl values ranging from about 10 to about 40%, and a molecular weight of about 15,000 to about 75,000; C-A-T having trimellityl values of about 15 to about 30%; C-A-S having succinyl value of about 15 to about 40%; and HPMCP having phthalyl values of about 25% to about 35%, and a molecular weight of 30,000 to 100,000. Other cellulosic polymers such as HPMCAS (Hydroxypropyl methyl cellulose acetate succinate) and CMEC (carboxy methyl ethyl cellulose) can also be used. An aqueous coating solution can be prepared by dispersing a cellulosic enteric polymer such as HPMCP in distilled water, and then adding ammonium hydroxide (30% $NH_3$ by wt) or sodium hydroxide to the dispersion and stirring until all particles are dissolved. A 10% HPMCP solution typically has a pH value of about 5.5 and a viscosity value of about 45 cps.

Thus, the present invention provides an aqueous enteric coating composition, which comprises a blend of an alkali-soluble acrylic polymer latex and an ammonium or alkaline salt solution of a cellulosic enteric polymer, wherein the composition consists of:

(a) 1 to 35% by weight of an alkali-soluble acrylic latex polymer emulsion, (b) 1 to 25% by weight of ammonium or alkaline salts of a cellulosic enteric polymer, and (c) 60 to 95% by weight of water.

In accordance with this invention, it is preferred that the total polymer concentration (i.e., (a) and (b) above) reside in the range of about 5% to about 25% of the blend by weight. Preferably the total polymer concentration should be in the range of about 10% to about 20%. Further, it is preferred that the acrylic polymer be a copolymer of either copoly (methacrylic acid/ethyl acrylate, 1:1), or copoly(methacrylic acid/methyl acrylate, 1:1). Preferred cellulosic polymers are HPMCP and C-A-P. The most preferred blend comprises copoly(methacrylic acid/ethyl acrylate, 1:1) and ammonium or sodium salts of HPMCP. Plasticizers, pigments, colorants, antifoam agents, antioxidants, waxes, monoglycerides, emulsifiers, surfactants and other additives can be added to the dispersion (i.e., the blend) either to adjust its viscosity or to modify the resultant film properties.

As noted above, it is a further aspect of this invention to provide a method for preparing the present enteric coating compositions. Thus, in preparing a coating composition according to this invention, an amount of aqueous ammonium salt solution of a cellulosic enteric polymer is slowly admixed with the alkali-soluble acrylic polymer latex. Additives may be incorporated before the blending either in the latex or in the ammonium salt solution of a cellulosic enteric polymer.

In addition it is a further aspect of this invention to provide a method for coating a dosage form with the present compositions. The compositions of the present invention can be used preferably to coat active ingredients in a solid dosage form such as tablets, beads, granules, or capsules having sufficient integrity and particle size by methodology known in the art. Typical coating methods for applying enteric polymers are fluidized bed and side vented pan coating processes. In these processes, a coating formulation containing the enteric polymer blend and possibly other materials such as plasticizers and fillers are applied via spray nozzles onto the dosage forms. The dosage form is fluidized with heated air or agitated by a rotating pan with heated air while applying the coating to prevent agglomeration and in order to dry the polymer film. Both processes result in a uniform film being applied to the surface of the active ingredient. The release of the active ingredient is controlled by the coating thickness, additives in the coating, the solubility of the active ingredient, and acidity or basicity of the extracting medium.

Embodiments of this invention are illustrated, but in no way limited, by the following examples.

EXAMPLE 1

This example illustrates that adding ammonium salts of HPMCP increases the tolerance of an alkali-soluble acrylic polymer latex for high shearing forces and heat associated with the admixing process.

A 10% by weight ammonium salt solution of HPMCP was prepared by dispersing HPMCP in water, adding enough ammonium hydroxide (30% $NH_3$) to 100% neutralize the acidic functional groups of HPMCP, and then adjusting the total amount of water to yield a 10% by weight polymer solution.

An amount of 200 mL Eastacryl® L 30 D latex was placed in a Waring® blender and subjected to high shearing agitation at a low speed setting. The latex emulsion coagulated to form a solidified mass in about 6 minutes at ambient temperature. Similarly Eudragit® L 30 D subjected to the same agitation coagulated in about the same time.

Eastacryl® L 30 D latex was diluted with water to yield a latex emulsion containing 10% polymer solid. 200 mL of the dilute emulsion was placed in the blender and subjected to high shearing agitation as described. The latex emulsion coagulated to form a gel mass in about 8 minutes.

20 mL of the 10% ammonium salt solution of HPMCP was slowly added to 180 mL of the dilute latex emulsion, and the blend was then subjected to the same high shearing agitation as described. The blend coagulated after about 20 minutes at 58° C. In another experiment, 40 mL of 10% ammonium salt solution of HPMCP was slowly added to 160 mL of the dilute latex emulsion. The blend was then subjected to the same high shearing agitation as described. The blend did not coagulate after about 25 minutes at about 60° C.

It is evident that a small amount of ammonium salts of a cellulosic polymer such as HPMCP can increase the tolerance of alkali-soluble acrylic latex emulsion for high shearing agitation and heat associated with the agitation. This discovery is particularly useful for preparing a water-dispersible powder product from an alkali-soluble acrylic polymer latex emulsion. The practice of making a water-dispersible product from the blends is described in Example 9.

EXAMPLE 2

This example illustrates that the blends described in this invention will minimize settling of talc particles in a coating dope.

A series of binary blends of copoly(methacrylic acid/ethyl acrylate 1:1) latex and ammonium salts of HPMCP (ammoniated HPMCP, or $NH_4HPMCP$) were made according to the description of this invention. A 10% by weight ammonium salt solution of HPMCP was prepared by dispersing HPMCP in water, adding enough ammonium hydroxide (30% $NH_3$) to 100% neutralize the acidic functional groups of HPMCP, and then adjusting the amount of water to yield a 10% polymer solution. The binary blends were made by adding 10% ammonium salt solution of HPMCP to 10% Eastacryl® 30 D at various ratios to form a 10%, by weight, polymer solution. The viscosity value of each blend was then measured using a digital Brookfield® viscometer using spindle No. 1. In another experiment, a small amount of talc, 2.5 gram (25% of polymer weight), was added to 100 mL of the blend, and then vigorously agitated to disperse talc particles. Similarly, 2.5 gram of talc was added to 100 mL of water and vigorously agitated to disperse talc particles. Each dispersion was placed in a graduated cylinder and allowed talc particles to settle. The volume of settled talc was measured after a period of time. The results are shown as follows:

| Ratio of Acrylic Latex/Ammoniated | Viscosity | Volume of Settled Talc mL | |
|---|---|---|---|
| HPMCP | CPS | 8 hr. | 16 hrs. |
| Talc in Water | — | 3.0 | 3.0mL |
| 100/0 | 5.12 | 5.0 | 6.0 |
| 90/10 | 8.32 | 5.0 | 5.0 |
| 80/20 | 13.4 | 4.0 | 4.5 |
| 70/30 | 17.9 | 1.0 | 3.0 |
| 60/40 | 21.1 | 1.5 | 1.5 |
| 50/50 | 21.8 | 1.5 | 1.0 |
| 40/60 | 23.7 | 1.0 | 1.0 |
| 30/70 | 26.9 | 1.5 | 1.0 |
| 20/80 | 32.6 | 1.0 | 1.0 |
| 10/90 | 39.0 | 1.0 | 1.0 |
| 0/100 | 45.0 | 0.5 | 0.5 |

These data illustrate that a) talc particles in water settle rather quickly to form a layer of dense precipitate, b) the degree of talc settlement in 10% acrylic emulsion is even higher than talc in water, c) talc in 10% ammonium salt solution of HPMCP exhibits a minimum degree of settlement, d) increasing ammoniated HPMCP in acrylic emulsion prolongs the suspension of talc particles in the blend.

EXAMPLE 3

This example illustrates the constancy of pH values for the blends as given in Example 2.

| Ratio of Acrylic Latex/<br>Ammoniated HPMCP | pH Values |
|---|---|
| 100/0 (10% solid) | 2.92 |
| 90/10 | 4.68 |
| 80/20 | 4.72 |
| 70/30 | 4.73 |
| 60/40 | 4.74 |
| 50/50 | 4.74 |
| 40/60 | 4.77 |
| 30/70 | 4.77 |
| 20/80 | 4.78 |
| 10/90 | 4.80 |
| 0/100 | 4.82 |

These data suggests that a blend of alkali-soluble acrylic latex emulsion and ammonium salt solution of HPMCP exhibits buffer capacity to minimize any pH shocks due to acids or bases added to the coating preparation.

EXAMPLE 4

This example further illustrates the viscosity and pH differences for four coating dopes containing Eastacryl® 30 D acrylic latex and ammoniated HPMCP blends, talc at a level of 25% acrylic latex polymer weight, and triethyl citrate as a plasticizer at a level of 0, 5, and 10% total polymer weight.

| Acrylic Latex/<br>NH$_4$HPMCP | pH Values<br>at Three Pz levels | | | Viscosity, cPS<br>at Three pZ levels | | |
|---|---|---|---|---|---|---|
| Ratio (w/w) | 0 | 5 | 10 | 0 | 5 | 10 |
| 100/10 | 3.24 | 3.23 | 3.28 | 4.2 | 5.1 | 2.4 |
| 75/25 | 4.84 | 4.92 | 4.93 | 25.8 | 17.6 | 12.6 |
| 50/50 | 4.89 | 4.98 | 5.03 | 42.0 | 30.0 | 22.8 |
| 25/75 | 4.98 | 5.07 | 5.14 | 45.6 | 38.4 | 33.6 |
| 0/100 | 5.11 | 5.28 | 5.40 | 62.4 | 51.0 | 45.0 |

It is evident that these blends exhibit buffer capacity and significantly higher viscosity values so that rapid settling of talc particles in the coating dope can be avoided. The blends without plasticizer also exhibit a viscosity value higher than the corresponding blend with the presence of a plasticizer.

EXAMPLE 5

This example shows the minimum film forming temperatures (MFFT) for a series of acrylic latex/ammoniated HPMCP blends as given in Example 1, and compares Tg's of the blends with alkali-soluble acrylic latex emulsion plasticized with typical plasticizers such as diethyl phthalate (DEP), triacetin, and triethyl citrate (TEC) at 10 and 20% of the weight of polymeric blends.

| Ratio of Acrylic Latex/<br>Ammoniated HPMCP | MFT, °C. |
|---|---|
| 100/0 (10% solid) | 27 |
| 100/0 with | |
| 10% DEP | 6 |
| 20% DEP | <0 |
| 100/0 with | |
| 10% triacetin | <0 |
| 20% triacetin | <0 |
| 100/0 with | |
| 10% TEC | <0 |
| 20% TEC | <0 |
| 90/10 | <0 |
| 80/20 | <0 |
| 70/30 | <0 |
| 60/40 | <0 |
| 50/50 | <0 |
| 40/60 | <0 |
| 30/70 | <0 |
| 20/80 | <0 |
| 10/90 | <0 |
| 0/100 | <0 |

It is evident that addition of ammonium salts of HPMCP to alkali-soluble acrylic latex lowered the minimum film forming temperatures of the blends just as the conventional plasticizers. Thus ammonium salts of HPMCP can be used as a "polymeric enteric plasticizer" for alkali-soluble acrylic latex emulsions for enteric coating applications.

EXAMPLE 6

This example shows the glass transition temperatures of the blends. Theophylline tablets (200 mg) were first coated with a layer of hydroxypropyl methyl cellulose (HPMC) to a coating level of approximately 0.8% of the tablet weight, and then coated with a layer of enteric coating using the dopes (15 in total) as given in Example 3 to a level of 10% of the tablet weight. The residual ammonium ion content in a coating film was analyzed by an ion chromatography method. Results are shown in the following table.

| Blend Ratio | Residual NH$_4^+$ in the Film | | |
|---|---|---|---|
| Latex/NH$_4$HPMCP | 0 | 5 | 10 |
| 100/0 | 0.02 | 0.02 | 0.02 |
| 75/25 | 0.95 | 1.02 | 0.93 |
| 50/50 | 1.79 | 1.80 | 1.41 |
| 25/75 | 2.40 | 2.12 | 2.15 |
| 0/100 | 2.71 | 2.67 | 2.61 |

These data indicate that the residual ammonium ion in coating film at the given coating condition was less than 3.6%, by weight, of the coating film, which is the stoichiometric amount of 100% neutralized ammonium salts of HPMCP.

After storing coated tablets at an ambient condition and at an accelerated condition, 40° C. and 75% relative humidity, for 90 days, the coatings from the tablets were then peeled off for analysis of the glass transition temperatures by a differential scanning calorimetry (DSC) method. The glass transition temperature of HPMC subcoat alone was determined to be 56° C. But because of the small quantity of HPMC in the overall coating, the Tg of the subcoat in the composite coating was not detectable. Only one Tg detected for each blend. This is a strong indication that the enteric acrylic polymer is miscible with ammonium salts of HPMCP. The Tg values of the blends are shown in the following table:

| Blend Ratio Acrylic/ NH4HP | Tg (Film at ambient cond.) | | | Tg (Film at 40° C./75RH) | | |
|---|---|---|---|---|---|---|
| | 0 | 5 | 10, % Pz | 0 | 5 | 10, % Pz |
| 100/0 | 112 | 101 | 86 | 113 | 100 | 84 |
| 75/25 | 90 | 76 | 74 | 90 | 79 | 72 |
| 50/50 | 80 | — | — | 80 | — | — |
| 25/75 | 79 | — | — | 81 | — | — |
| 0/100 | 80 | 66 | 61 | — | 68 | 65 |

These data indicate that the blends exhibit a lower Tg than the acrylic latex alone even without plasticizers. Thus ammonium salts of HPMCP can be used as an enteric polymeric plasticizer to lower Tg of an enteric acrylic latex so as to give a more flexible coating film. The improved flexibility and elasticity would allow coated substrates such granules, beads, or pellets to withstand high compacting forces in a tableting process.

The film surfaces of the blends without plasticizer were analyzed by scanning electron microscopy. The micrographs clearly indicated that the surface of the film made from acrylic latex exhibits pin holes, but the surfaces of the films made of the blends do not show pinholes.

EXAMPLE 7

Theophylline tablets described in Example 5 were evaluated for their integrity in simulated gastric fluid at pH 1.2 for 90 min. and then evaluated for disintegration in simulated intestinal fluid at pH 6.8. All of the freshly prepared tablets and tablets stored at an accelerated condition, 40° C. and 75% RH, for a period of time from 30 to 90 days remained enterically protected at pH 1.2, but disintegrated within 30 minutes at pH 6.8. The results are shown in the following tables, A, B, and C.

| Blend Ratio Acrylic/NH4HPMCP | Disintegration time, minutes | | | |
|---|---|---|---|---|
| | 0- | 31- | 60- | 90-days |
| A: Coating without plasticizer | | | | |
| 100/0 | 27 | 24 | 22 | 27 |
| 75/25 | 12 | 24 | 17 | — |
| 50/50 | 9 | 15 | 16 | 17 |
| 25/75 | 9 | 13 | 14 | 15 |
| 0/100 | 8 | 10 | 9 | 19 |
| B: Coating with 5% plasticizer (TEC) | | | | |
| 100/0 | 26 | 28 | 35 | 26 |
| 75/25 | 24 | 25 | 20 | 19 |
| 50/50 | 21 | 19 | 13 | 16 |
| 25/75 | 9 | 14 | 14 | — |
| 0/100 | 8 | 12 | — | — |
| C: Coating with 10% plasticizer (TEC) | | | | |
| 100/0 | 26 | 32 | 27 | 25 |
| 75/25 | 13 | 23 | 19 | 19 |
| 50/50 | 12 | 16 | 13 | 15 |
| 25/75 | 9 | 10 | 8 | — |
| 0/100 | — | 7 | 10 | — |

EXAMPLE 8

This example shows that addition of up to 25% of ammonium salt solution of HPMCP to an alkali-soluble acrylic latex emulsion does not adversely affect the long term stability of the tablets subjected to accelerated stability test conditions.

Theophylline tablets given in Example 6 C, coating with 10% plasticizer, were evaluated for uptake of gastric fluid after a period of storage time (0–90 days) at the accelerated condition. The total uptake of gastric fluid was determined to be less than 5% of the tablet weight. Results are shown in the following table:

| Blend Ratio Latex/ NH4HP | Gastric Uptake, wt % | | | | Disintegration time, min. | | | |
|---|---|---|---|---|---|---|---|---|
| | 0- | 31- | 60- | 90-days | 0- | 31- | 60- | 90-days |
| 100/0 | 1.54 | 3.83 | 1.58 | 1.60 | 26 | 32 | 27 | 25 |
| 75/25 | 2.84 | 3.34 | 3.43 | 3.78 | 13 | 23 | 19 | 19 |
| 50/50 | 9.87 | 5.44 | 12.4 | 52.4 | 12 | 16 | 13 | 15 |
| 25/75 | 14.5 | 38.6 | 44.8 | — | 9 | 10 | 8 | — |
| 0/100 | 27.5 | 41.0 | — | — | — | 7 | 10 | — |

It is shown that if the ammonium salt concentration in the blend was less than 25% of the total polymer weight, the gastric fluid uptake into the tablet was less than 5% by weight.

EXAMPLE 9

The results given in Example 1 indicate that ammonium salts of HPMCP can be used as a protective colloid to increase the tolerance of alkali-soluble acrylic latex emulsion to shear and heat. This example shows that this finding can be used in a process for producing a water-dispersible powdered product from alkali-soluble acrylic latex emulsion via a spray drying process.

Since alkali-soluble acrylic latex has a relatively low minimum film forming temperature and a low Tg, it is an inherent property that the latex emulsion will coagulate when subjected to high shear and heat. Typically in a spray drying process, an emulsion or suspension is necessarily subjected to high shear through the spraying nozzle, and heat in the system to evaporate water. Thus, in spray drying a latex emulsion, it is critical to adjust the product and process temperatures as well as the spraying rate to lower levels that optimum conditions to produce the desired powder product. The delicacy of the process may cause low efficiency in the spray dryer resulting in a lower production rate. The addition of ammonium or alkaline salt solution of a cellulosic enteric coating polymer to an alkali-soluble acrylic latex emulsion may improve the process conditions to allow the spraying process at a higher temperature and higher spraying rate. Typically spray drying of a blend of alkali-soluble acrylic latex emulsion and ammonium salt solution of HPMCP can be done, but not limited to, using a tower spray dryer. For a typical "Roger" spray dryer, (40 ft in height, 6 ft in diameter, equipped with a high pressure nozzle), the typical conditions are given as follows:

Product feed temperature: 50°–70° C.

Inlet air temperature: 75°–85° C.

Nozzle Pressure: 1000 psi.

The yield of spraying 100 Kg acrylic latex at 10–30% solid is greater than about 80%.

The invention has been described in detail with particular reference to preferred embodiments thereof, but it will be understood that variations and modifications can be effected within the spirit and scope of the invention.

We claim:

1. An enteric coating composition comprising a dispersion of
   a) an alkali-soluble acrylic latex polymer suspended in
   b) an aqueous solution of ammonium or alkaline salts of cellulose polymers.

2. An enteric coating composition according to claim 1 wherein the composition comprises
   a) about 1 to about 35% by weight of the alkali-soluble acrylic latex polymer;
   b) about 1 to about 25% by weight of the ammonium or alkaline salts of the cellulosic polymers; and
   c) about 60 to about 95% by weight of water.

3. An enteric coating composition as claimed in claim 2 wherein the total of components a) and b) is about 5 to about 25%.

4. An enteric coating composition according to claim 1 wherein the alkali-soluble acrylic latex polymer is a latex emulsion of copolymers of acrylic acid monomers and acrylate monomers.

5. An enteric coating composition according to claim 4 wherein the copolymer component a) is copolymer (methacrylic acid/ethyl acrylate), copoly(methacrylic acid/methyl methacrylate), or a combination of methacrylic acid, methyl methacrylate and ethyl acrylate.

6. An enteric coating composition according to claim 4 wherein the cellulosic polymer component b) is cellulose acetate phthalate, cellulose acetate trimellitate, cellulose acetate succinate, hydroxypropyl methyl cellulose phthalate, carboxymethyl ethyl cellulose or hydroxypropyl methyl cellulose acetate succinate.

7. An enteric coating composition according to claim 6 wherein component a) is copoly(methacrylic acid/methyl acrylate) or copoly(methacrylic acid/methyl acrylate) and component b) is hydroxy propyl methyl cellulose phthalate or cellulose acetate phthalate.

8. An enteric coating composition according to claim 7 wherein component a) is copoly(methacrylic acid/ethyl acrylate and component b) is hydroxypropyl methyl cellulose phthalate.

9. An enteric coating composition according to claim 1 wherein the dispersion further comprises at least one of a plasticizer, a pigment, a colorant, an antifoam agent, an antioxidant, a wax, a monoglyceride, an emulsifier or a surfactant.

10. A method for preparing an enterically-coated solid dosage form which comprises contacting the dosage form with an enteric coating composition comprising a dispersion of
    a) about 1 to about 35% weight of an alkali-soluble acrylic latex polymer suspended in;
    b) about 1 to about 25% by weight of an aqueous solution of ammonium or alkaline salts of cellulose polymers; and
    c) about 60 to about 95% by weight of water.

11. A method as claimed in claim 10 wherein the contacting is accomplished in a fluidized bed coater or a side-vented pan coater.

12. A method as claimed in claim 11 wherein component a) is copolymer(methacrylic acid/ethyl acrylate), copoly (methacrylic acid/methyl methacrylate), or a combination of methacrylic acid, methyl methacrylate and ethyl acrylate.

13. A method as claimed in claim 11 wherein component b) is cellulose acetate phthalate, cellulose acetate trimellitate, cellulose acetate succinate, hydroxypropyl methyl cellulose phthalate, carboxymethyl ethyl cellulose or hydroxypropyl methyl cellulose acetate succinate.

14. A method as claimed in claim 11 wherein component a) is copoly(methacrylic acid/ethyl acrylate) or copoly (methacrylic acid/methyl acrylate) and component b) is hydroxy propyl methyl cellulose phthalate or cellulose acetate phthalate.

15. A method as claimed in claim 14 wherein component a) is copoly(methacrylic acid/ethyl acrylate and component b) is hydroxypropyl methyl cellulose phthalate.

16. A method as claimed in claim 10 wherein the composition further comprises at least one of a plasticizer, a pigment, a colorant, an antifoam agent, an antioxidant, a wax, a monoglyceride, an emulsifier or a surfactant.

17. A method for preparing an enteric coating composition which comprises blending an alkali-soluble acrylic latex polymer and an ammonium or alkaline salt of a cellulosic polymer.

* * * * *